(12) United States Patent
Tombari et al.

(10) Patent No.: US 8,153,648 B2
(45) Date of Patent: Apr. 10, 2012

(54) SOLID AND CRYSTALLINE DUTASTERIDE AND PROCESSES FOR PREPARATION THEREOF

(75) Inventors: Dora Graciela Tombari, Buenos Aires (AR); Constanza Pia Mangone, Buenos Aires (AR); Maria Beatriz Garcia, Buenos Aires (AR); Adriana Vechhioli, Buenos Aires (AR); Rafael Alberto Labriola, Beccar (AR)

(73) Assignee: Gador S.A., Buenos Aires (AR)

( * ) Notice: Subject to any disclaimer, the term of this patent is extended or adjusted under 35 U.S.C. 154(b) by 622 days.

(21) Appl. No.: 12/348,278

(22) Filed: Jan. 3, 2009

(65) Prior Publication Data

US 2009/0203724 A1  Aug. 13, 2009

Related U.S. Application Data (60) Provisional application No. 61/018,808, filed on Jan. 3, 2008.

(51) Int. Cl.
*A61K 31/473* (2006.01)
*C07D 221/18* (2006.01)

(52) U.S. Cl. .......................................... 514/284; 546/77

(58) Field of Classification Search .................. 514/284; 546/77

See application file for complete search history.

(56) References Cited

U.S. PATENT DOCUMENTS

| 5,565,467 | A | 10/1996 | Batchelor et al. |
| 7,022,854 | B2 * | 4/2006 | Reddy et al. .................... 546/77 |
| 2004/0077673 | A1 | 4/2004 | Reddy et al. |
| 2006/0100434 | A1 | 5/2006 | Scharer et al. |

FOREIGN PATENT DOCUMENTS

| WO | 9507927 A1 | 3/1995 |
| WO | 0246207 A2 | 6/2002 |
| WO | 2004007523 A1 | 1/2004 |

* cited by examiner

*Primary Examiner* — Charanjit Aulakh
(74) *Attorney, Agent, or Firm* — Patent Central LLC; Stephan A. Pendorf (57) ABSTRACT

The solid state chemistry of 17β-N-[2,5-bis(trifluoromethyl)phenyl]carbamoyl-4-aza-5-α-androst-1-en-3-one of which the international nonproprietary name is Dutasteride (the active ingredient in products marketed as Avodart, Avidart, Avolve, Duagen, Dutas, Dutagen, Duprost) and its process for preparing. The synthetic process comprises formation of the mixed anhydride, its subsequent reaction with 2,5-bis(trifluoromethyl)phenylamine in the presence of an appropriate Lewis catalyst and its isolation, purification and crystallization from acetonitrile/water.

45 Claims, 6 Drawing Sheets

Fig. 1A

DESCRIPTION:
bfi12516

ORIGINAL SCAN: bfi12516
SCAN CREATED: 02/07/2007 06:26
DESCRIPTION OF SCAN:
bfi12516

*Fig. 1B*

USED WAVELENGTH: K-ALPHA
WAVELENGTH (Å): 1.54060
PEAK SEARCH PARAMETER SET: AS MEASURED INTENSITIES
SET CREATED: 30/08/2004 11:06
PEAK POSITIONED DEFINED BY: MINIMUM OF 2ND DERIVATIVE
MINIMUM PEAK TIP WIDTH (°2 THETA) 0.00
MAXIMUM PEAK TIP WIDTH (°2 THETA) 1.00
PEAK BASE WIDTH (°2 THETA) 2.00
MINIMUM SIGNIFICANCE 0.75

| d-SPACING (Å) | RELATIVE INTENSITY (%) | RELATIVE (°2 THETA) | PEAK HEIGHT (COUNTS) | BACKGROUND (COUNTS) | TIP WIDTH (°2 THETA) | SIGNIFICANCE |
|---|---|---|---|---|---|---|
| 16.21346 | 2.37 | 5.44629 | 644.81 | 98.06 | 0.18000 | 13.94 |
| 12.66373 | 0.59 | 6.97459 | 160.23 | 98.06 | 0.08000 | 0.93 |
| 9.80658 | 1.03 | 9.01037 | 280.44 | 98.06 | 0.12000 | 3.23 |
| 9.21685 | 2.50 | 9.58820 | 681.50 | 98.06 | 0.14000 | 5.82 |
| 8.92789 | 3.19 | 9.89929 | 868.77 | 98.06 | 0.16000 | 9.44 |
| 7.99292 | 2.46 | 11.06068 | 669.87 | 98.06 | 0.14000 | 6.86 |
| 7.32659 | 1.85 | 12.07018 | 503.80 | 98.06 | 0.10000 | 2.93 |
| 6.13463 | 10.08 | 14.42687 | 2746.77 | 98.06 | 0.24000 | 23.36 |
| 6.03715 | 6.65 | 14.66109 | 1811.63 | 98.06 | 0.12000 | 4.51 |
| 5.68629 | 6.23 | 15.57115 | 1699.50 | 98.06 | 0.18000 | 16.76 |
| 5.44687 | 1.77 | 16.26013 | 482.86 | 98.06 | 0.12000 | 3.11 |
| 5.11996 | 1.62 | 17.30606 | 441.21 | 98.06 | 0.12000 | 2.09 |
| 5.02773 | 2.92 | 17.62603 | 794.69 | 98.06 | 0.10000 | 2.28 |
| 4.87786 | 2.09 | 18.17208 | 568.75 | 98.06 | 0.20000 | 1.76 |
| 4.62359 | 100.00 | 19.18062 | 27260.29 | 98.06 | 0.18000 | 77.30 |
| 4.56678 | 26.45 | 19.42152 | 7210.52 | 98.06 | 0.18000 | 1.76 |
| 4.47741 | 3.44 | 19.81308 | 936.51 | 98.06 | 0.18000 | 5.87 |
| 4.29927 | 5.71 | 20.64282 | 1557.28 | 98.06 | 0.20000 | 17.46 |
| 4.11079 | 1.29 | 21.60040 | 352.22 | 98.06 | 0.16000 | 1.27 |
| 4.00051 | 2.04 | 22.20333 | 555.31 | 98.06 | 0.10000 | 1.13 |
| 3.80193 | 3.63 | 23.37895 | 989.16 | 98.06 | 0.14000 | 3.22 |
| 3.57362 | 1.37 | 24.89579 | 373.37 | 98.06 | 0.20000 | 2.27 |
| 3.48795 | 2.44 | 25.51747 | 665.44 | 98.06 | 0.12000 | 2.07 |
| 3.30876 | 4.58 | 26.92467 | 1249.63 | 98.06 | 0.12000 | 2.87 |
| 3.12703 | 2.51 | 28.52161 | 685.06 | 98.06 | 0.12000 | 1.30 |
| 3.08244 | 4.32 | 28.94311 | 1177.73 | 98.06 | 0.14000 | 3.88 |
| 2.96583 | 1.66 | 30.10749 | 451.24 | 98.06 | 0.28000 | 4.90 |
| 2.88233 | 1.90 | 31.00128 | 517.74 | 98.06 | 0.12000 | 1.46 |

| d-SPACING (Å) | RELATIVE INTENSITY (%) | RELATIVE (°2 THETA) | PEAK HEIGHT (COUNTS) | BACKGROUND (COUNTS) | TIP WIDTH (°2 THETA) | SIGNIFICANCE |
|---|---|---|---|---|---|---|
| 2.82012 | 1.74 | 31.70298 | 473.54 | 98.06 | 0.12000 | 13.94 |
| 2.71421 | 1.41 | 32.97458 | 384.71 | 98.06 | 0.20000 | 0.93 |
| 2.67060 | 1.19 | 33.52878 | 324.29 | 98.06 | 0.10000 | 3.23 |
| 2.63338 | 1.06 | 34.01707 | 288.74 | 98.06 | 0.16000 | 5.82 |
| 2.52403 | 1.21 | 35.53881 | 329.51 | 98.06 | 0.32000 | 9.44 |
| 2.46026 | 1.42 | 36.49190 | 387.87 | 98.06 | 0.20000 | 6.86 |
| 2.40859 | 1.09 | 37.30324 | 298.15 | 98.06 | 0.20000 | 2.93 |
| 2.35853 | 1.43 | 38.12527 | 389.10 | 98.06 | 0.24000 | 23.36 |
| 2.30922 | 2.11 | 38.97200 | 575.36 | 98.06 | 0.20000 | 4.51 |
| 2.29233 | 1.58 | 39.27084 | 429.93 | 98.06 | 0.28000 | 16.76 |

| NO. | ABSCISSA | PEAK HEIGHT | ABSCISSA BASE |
|---|---|---|---|
| 1 | 3464.7 | 55.82 | 14.27 |
| 2 | 3428.0 | 65.13 | 2.42 |
| 3 | 3202.3 | 61.63 | 14.35 |
| 4 | 3100.1 | 81.00 | 3.04 |
| 5 | 3048.0 | 81.20 | 5.64 |
| 6 | 2972.8 | 64.43 | 3.54 |
| 7 | 2941.9 | 43.49 | 21.93 |
| 8 | 2872.5 | 64.98 | 7.45 |
| 9 | 2855.1 | 69.83 | 4.17 |
| 10 | 2361.2 | 100.42 | 2.60 |
| 11 | 1919.5 | 97.37 | 1.31 |
| 12 | 1716.9 | 42.04 | 11.60 |
| 13 | 1693.8 | 27.20 | 2.58 |
| 14 | 1674.5 | 5.00 | 35.42 |
| 15 | 1593.5 | 27.20 | 51.98 |
| 16 | 1533.7 | 38.45 | 40.92 |
| 17 | 1471.9 | 49.40 | 8.18 |
| 18 | 1433.3 | 10.40 | 51.90 |
| 19 | 1392.8 | 62.06 | 11.76 |
| 20 | 1365.8 | 58.14 | 12.64 |
| 21 | 1333.0 | 22.56 | 14.38 |
| 22 | 1317.6 | 6.18 | 32.78 |
| 23 | 1263.0 | 16.62 | 46.85 |
| 24 | 1238.5 | 44.51 | 16.41 |
| 25 | 1221.1 | 59.72 | 7.46 |
| 26 | 1178.7 | 11.76 | 29.94 |
| 27 | 1145.9 | 7.43 | 9.60 |
| 28 | 1128.5 | 6.88 | 9.93 |
| 29 | 1086.1 | 18.15 | 44.92 |
| 30 | 1041.7 | 38.03 | 47.47 |
| 31 | 970.3 | 85.57 | 4.11 |
| 32 | 960.7 | 83.30 | 5.67 |
| 33 | 939.5 | 77.75 | 7.77 |
| 34 | 926.0 | 81.62 | 2.58 |
| 35 | 900.6 | 66.79 | 17.13 |
| 36 | 962.3 | 85.76 | 3.48 |
| 37 | 831.5 | 51.54 | 6.54 |
| 38 | 823.7 | 42.47 | 15.37 |
| 39 | 746.6 | 68.13 | 16.48 |
| 40 | 694.5 | 73.41 | 2.14 |
| 41 | 671.3 | 68.00 | 5.47 |
| 42 | 661.7 | 70.02 | 3.70 |
| 43 | 607.7 | 73.67 | 4.08 |
| 44 | 561.4 | 70.74 | 1.82 |
| 45 | 542.1 | 70.26 | 1.04 |
| 46 | 530.5 | 68.42 | 2.80 |
| 47 | 515.1 | 68.45 | 4.81 |
| 48 | 488.1 | 72.76 | 5.26 |
| 49 | 466.8 | 76.56 | 4.45 |
| 50 | 437.9 | 69.19 | 14.77 |

SOLID AND CRYSTALLINE DUTASTERIDE AND PROCESSES FOR PREPARATION THEREOF

FIELD OF THE INVENTION

The present invention relates to the solid state chemistry of 17β-N-[2,5-bis(trifluoromethyl)phenyl]carbamoyl-4-aza-5-α-androst-1-en-3-one of which the international nonproprietary name is Dutasteride (the active ingredient in products marketed as Avodart, Avidart, Avolve, Duagen, Dutas, Dutagen, Duprost) and its process for preparing. The synthetic process comprises the mixed anhydride formation, its subsequent reaction with 2,5-bis(trifluoromethyl)phenylamine in the presence of an appropriate Lewis catalyst and its isolation, purification and crystallization from acetonitrile/water.

Thus, the present invention is a novel polymorphic form of Dutasteride called form III, it also relates to methods for preparing Dutasteride in its polymorphic form III.

BACKGROUND OF THE INVENTION

The chemical structure of Dutasteride is the following:

DUTASTERIDE

Dutasteride is a selective inhibitor of the type 1 and type 2 isoforms of steroid 5α-reductase (5 AR), an intracellular enzyme that converts testosterone to 5α-dihydrotestosterone (DHT). Dutasteride is currently available in the market as Avodart, Avidart, Avolve, Duagen, Dutas, Dutagen, Duprost, etc. as a drug for benign prostatic hyperplasia, and is used for the treatment of prostate diseases such as prostate cancer, acne, male pattern baldness, hirsutism, and prostate gland enlargement.

The first reported synthetic methods for Dutasteride were described in WO 95/07927 and U.S. Pat. No. 5,565,467.

U.S. Pat. No. 5,565,467 shows two different ways to get Dutasteride, one of them includes dehydrogenation of 17β-N-[2,5-bis(trifluoromethyl)phenyl]carbamoyl-4-aza-5-α-androstane-3-one in the presence of catalysts 2,3-dichloro-5,6-dicyano-1,4-benzoquinone (DDQ) and bis(trimethylsilyl)trifluoroacetamide in dioxane as solvent. This process involves several steps.

The second option is more simple and starts from 4-aza-5α-androst-1-ene-3-one-17β-carboxylic acid. This second way to produce Dutasteride is similar to that disclosed in WO 95/07927.

It is important to note that, in both patents, the carboxylic group in 4-aza-5α-androst-1-ene-3-one-17β-carboxylic acid (II) (See Scheme 1) is transformed first into the corresponding acyl halide by thionyl chloride and after that it is transformed into the corresponding amide group. Both patents employ the same basic reagents but different conditions (See Table I). Only the patent WO 9507927 (1995) discloses a yield of 48%.

SCHEME 1

TABLE I

| Reagents to produce: | Document WO 9507927 - Example 2 | Document U.S. Pat. No. 5,565,467 - Example 2 |
|---|---|---|
| Acyl halide | Thionyl chloride Toluene DMF Pyridine | Thionyl chloride Pyridine |

TABLE I-continued

| Reagents to produce: | Document WO 9507927 - Example 2 | Document U.S. Pat. No. 5,565,467 - Example 2 |
|---|---|---|
| Time reaction | 2 hs | 2.5-3 hs |
| Amide group | 2,5-bis(trifluoro-methyl)phenylamine 4-dimethylamino pyridine | 2,5-bis(trifluoro-methyl)phenylamine |
| Time reaction | 15-16 hs | 4-6 hs |
| Global yield two steps | 48% | Not disclosed |

Afterwards, a modification of the same process (WO 9507927) in a large scale (18 kg) was disclosed in WO 02/46207 with a yield of 37-57%.

Other different process was disclosed in WO 2004/007523. This process has more steps and seems to be too complicated to be performed in industrial scale.

On the other hand, no information related to polymorphic forms is given in the mentioned patents. Only the U.S. Pat. No. 5,565,467 patent makes reference that many organic compounds can exist in more than one crystalline form, but no specific information related to Dutasteride is presented.

The polymorphic forms of Dutasteride are disclosed in US 2004/077673A1, where two crystalline and one amorphous forms are described. The crystalline forms are named I and II and they are characterized by their X-ray powder diffraction pattern and infrared spectra.

SUMMARY OF THE INVENTION

In accordance with the invention, a convenient one-pot procedure is reported for the preparation of Dutasteride from 4-aza-5α-androst-1-ene-3-one-17β-carboxylic acid (sulfonic-carboxylic (IV) or carboxylic (V)) which can be isolated or not, and after that it reacts with 2,5-bis(trifluoromethyl)phenylamine in the presence of a Lewis acid like $BF_3$, $BCl_3$, $AlCl_3$ to produce the desired Dutasteride.

It is important to mention that:

a) The reaction condition developed in the present invention makes it possible to recover the un-reacted starting material (4-aza-5α-androst-1-ene-3-one-17β-carboxylic acid (II)) with a good quality.

b) The 2,5-bis(trifluoromethyl)phenylamine molar ratio employed during the amide group formation is lower than the molar ratio employed in the aforementioned documents

IV

V

Mixed sulfonic-carboxylic anhydrides and mixed carboxylic anhydrides formally derived by elimination of one molecule of water from a carboxylic and sulfonic acid or two carboxylic acids (Scheme 2).

SCHEME 2

Mixed sulfonic-carboxylic anhydride

Mixed carboxylic anhydride

R1 = or ≠ R2          R1 ≠ R2

Thus, anhydrides can be formed from two molecules of an ordinary acid only if a dehydrating agent is present. Other synthesis of mixed anhydrides involves the reactions of sulfonyl chlorides or acyl halide with carboxylic acid salts. If a metallic salt is used, then $Na^+$, $K^+$ or $Ag^+$ are the most common cations, but more often, pyridine or another tertiary amine is added to the free acid and the salt thus formed is treated with the acyl halide. This last procedure appeared to be restricted to aryl-acyl chlorides (Justus Liebigs Ann. Chem. 688, 78 (1965)).

In the present invention we developed a simple alternative mode of syntheses of mixed anhydrides (sulfonic-carboxylic or carboxylic) which possess advantages of yield and simplicity of operation and more economically.

In this process acyl aliphatic chloride or sulfonyl chloride are made react with an aliphatic carboxylic acid in an aprotic solvent like acetonitrile or tetrahydrofuran at low temperature (−30 to 0° C.) and in the presence of 1,8-diazabicyclo[5.4.0] undec-7-ene (DBU) (Scheme 3). The complex formed by the nucleophilic attack of the carboxylic acid on the acid chloride loses hydrogen chloride readily to give the mixed acid anhydride (Buehler and Pearson, *Survey of Organic Synthesis*, Wiley-Interscience, Page 877 (Ed. 1970)). The HCl is trapped by DBU.

SCHEME 3

It is well known that the mixed anhydrides are susceptible to thermal decomposition (disproportionation) and/or hydrolysis. The thermal disproportionation has been reported in the literature (J. Chem. Soc., 5474 (1964)). During this process (Scheme 4), two molecules of the mixed anhydride obtained react to produce one molecule of the anhydride carboxylic acid arising from the 4-aza-5α-androst-1-ene-3-one-17β-carboxylic acid (II) which appears to be less reactive.

SCHEME 4

We found that the thermal disproportionation (Scheme 4) of the mixed anhydrides is minimized or avoided when the reaction is performed at −30 to 0° C., preferably from −20 to 0° C.

Another important factor to have in consideration is the solvent employed. To produce mixed sulfonic-carboxylic anhydrides (Compound IV) in high yield, solvents like acetonitrile have to be used and oxygenated solvents have to be avoided. In the case of the mixed carboxylic anhydrides (Compound V), solvents oxygenated like tetrahydrofuran are preferred.

It is known that different percent of disproportionation can be found (J. Org. Chem., 36, 528 (1971)) depending on the solvent characteristics (oxygenated or not).

SCHEME 5

Once obtained the mixed anhydride, it can be isolated or not. Although purification by crystallization from different solvents could be performed, we have found recrystallization to be unreliable as a means of purification, effecting partial hydrolysis. In general, mixed anhydrides could be used without further purification because the quality of the obtained anhydride is acceptable to continue with the process.

Another important aspect of this invention is related to the second step. In the second step the anhydride group is transformed to amide group by reaction between mixed anhydride and 2,5-bis(trifluoromethyl)phenylamine. This reaction consists in a substitution.

The amide group generation is performed in the presence of a Lewis acid like boron trifluoride etherate, aluminium trichloride, titanium tetra chloride, boron trichloride, etc.

Probably, the Lewis acid lets the formation of a complex with the mixed anhydride (See Scheme 6). This complex suffers the nucleophilic attack from the amine group arising from the 2,5-bis(trifluoromethyl)phenylamine to rend the desired Dutasteride.

Due to the reactivity of the anhydride intermediates and the developed conditions (presence of Lewis acid), the reaction (Scheme 6) is finished in around 2 to 4 hours. This is a very important improvement compared with the previous reported synthetic processes.

The previous yields reported for these two steps were around 37-57%. In our developed process the global yield is 70-72%.

Beside the new process to obtain Dutasteride, we are reporting a new crystalline form. This new solid phase is named Form III.

Polymorphism can be defined as the ability of the same chemical substance to exist in different crystalline structures. The different structures are referred to as polymorphs, polymorphic modifications or forms. The present invention provides crystalline Form III of Dutasteride and a process for its preparation. The crystalline Form III of Dutasteride is characterized by a Philips equipment X' Pert model with the unit PW3710. Scans were performed over the range of 5°-40° 2θ, at a 0.02° step size for 2 s per step.

Thermal analysis was determined through the TGA (Thermogravimetric Analysis) with a TGA Q-500 V6.4 (TA Instruments®)

The melting points result from the curves obtained through DSC (Differential Scanning Calorimetry) in a TA Instruments DSC-equipment at 10° C./min with a 30 ml/min nitrogen flow.

The infrared spectra were carried out in a Shimadzu FTIR-8 100 equipment, using a solid substance in the form of pellets with KBr.

SCHEME 6

IV
Mixed sulfonic-carboxylic anhydride
or
Mixed carboxylic anhydride
LEWIS ACID: $BF_3 \cdot Et_2O$ (I)
DUTASTERIDE

DESCRIPTION OF THE DRAWINGS

FIG. 1B quantifies peak data for the diffractogram of FIG. 1A.

DETAILED DESCRIPTION OF THE INVENTION

Dutasteride is prepared by a novel and advantageous method because of the global process yield and the quality of the obtained product.

In accordance with the simple method of the present invention, the first step consists in the reaction of 4-aza-5α-androst-1-ene-3-one-17β-3-carboxylic acid (II) with methanesulfonyl chloride, p-toluenesulfonyl chloride or pivaloyl chloride in the presence of DBU with the selected solvent to produce a mixed anhydride.

The organic solvent(s) which may be used in the present invention includes at least one solvent selected from the group consisting of tetrahydrofuran, dioxane, acetonitrile, toluene, dimethylacetamide and dimethylformamide, tetrahydrofuran and acetonitrile is most preferred. The reaction of the present invention may be carried out at a temperature in the range of −40 to 10° C. during 15-90 min, preferably −20 to 0° C. during 15-30 min.

Throughout the reaction, there is significant release of hydrogen chloride which is trapped by the DBU present in the reaction. Others similar bases could be employed in this step like pyridine, triethylamine, etc.

In the present invention, the mixed anhydride obtained could be isolated or not.

In accordance with the simple method of the present invention, the mixed anhydrides obtained can be used without previous purification in the next step.

Thus, in accordance with the present invention, the solution of the mixed anhydride obtained reacts with 2,5-bis(trifluoromethyl)aniline in the presence of a Lewis acid.

The Lewis acid which may be employed in the present invention includes a catalyst from the group consisting of boron trifluoride etherate, boron trichloride, aluminium trichloride, titanium tetrachloride, most preferably boron trifluoride etherate.

In a preferred embodiment of the present invention, the Lewis catalyst is added previous to the addition of the amine compound.

The reaction of this step may be carried out at a temperature in the range of 20 to 90° C., preferably 60-80° C.

The completion of the reaction is monitored by HPLC.

Once the reaction has been completed, the volume is reduced by distillation. Water at 25° C. is added and cooled down to 0-5° C. The filtered solid is dissolved at reflux in acetonitrile. It precipitates with water and cools. This procedure is repeated until the material that has not reacted is eliminate, which is then recuperated.

Alternatively, once the reaction has concluded, the reaction mix concentrates; the residue is taken from an organic solvent, such as methylene dichloride, toluene, ethyl acetate, most preferably ethyl acetate.

The organic layer is treated successively with aqueous solution of sodium bicarbonate and hydrochloric acid.

In the present invention, the organic solution containing the desired Dutasteride is concentrated in vacuum to rend a solid.

In another embodiment, the process for preparation of polymorphic Form III of Dutasteride includes:
a. Dissolving a crude form of Dutasteride in a polar organic solvent, such as acetonitrile, acetone, methanol, tetrahydrofuran, isopropanol, dioxane, preferably acetonitrile
b. Dropping or pouring the hot solution to ice water
c. Filtering the crystallized solid accompanied by drying the compound in conventional methods to afford the crystalline Form III of Dutasteride.

Figure 1A:
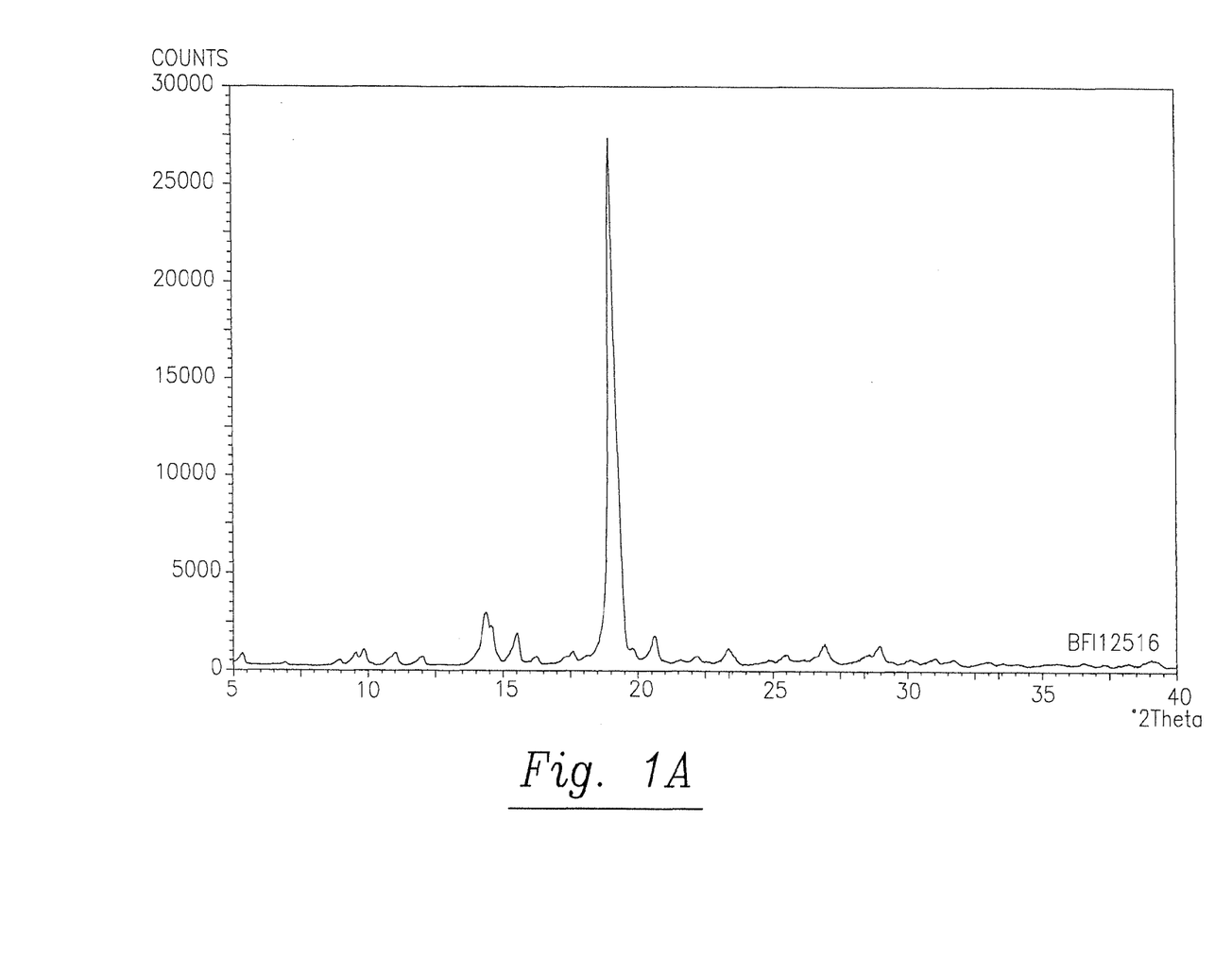
FIG. 1A shows an X-Ray powder diffractogram of crystalline Form III of Dutasteride.
Figure 1C:
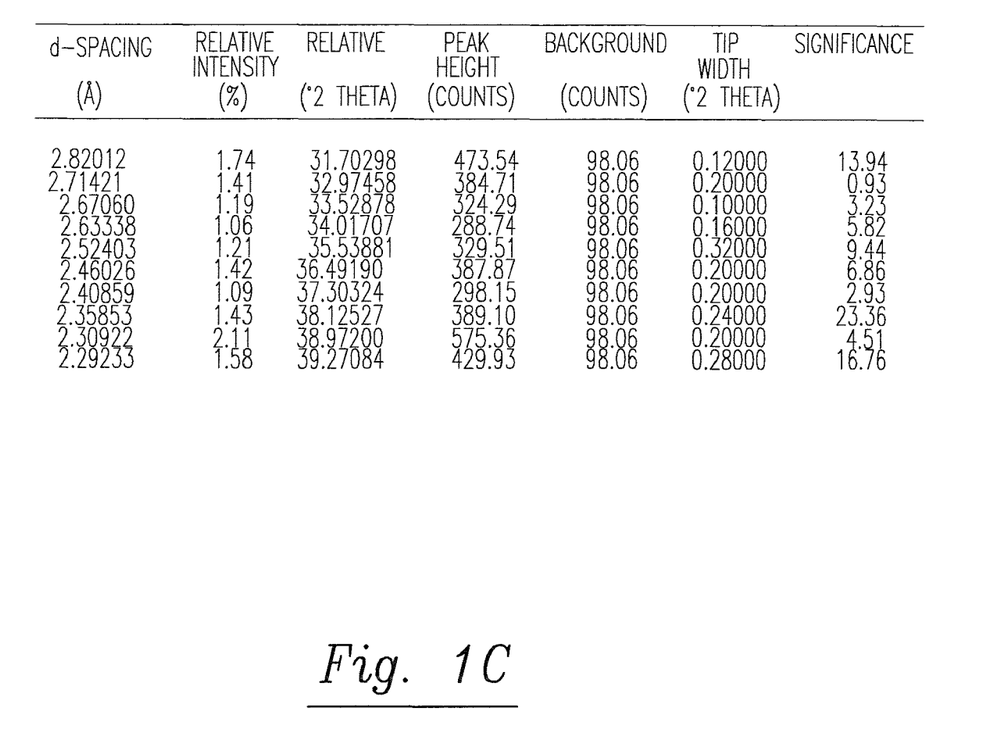
FIG. 1C is a continuation of FIG. 1B.
Figure 2A:
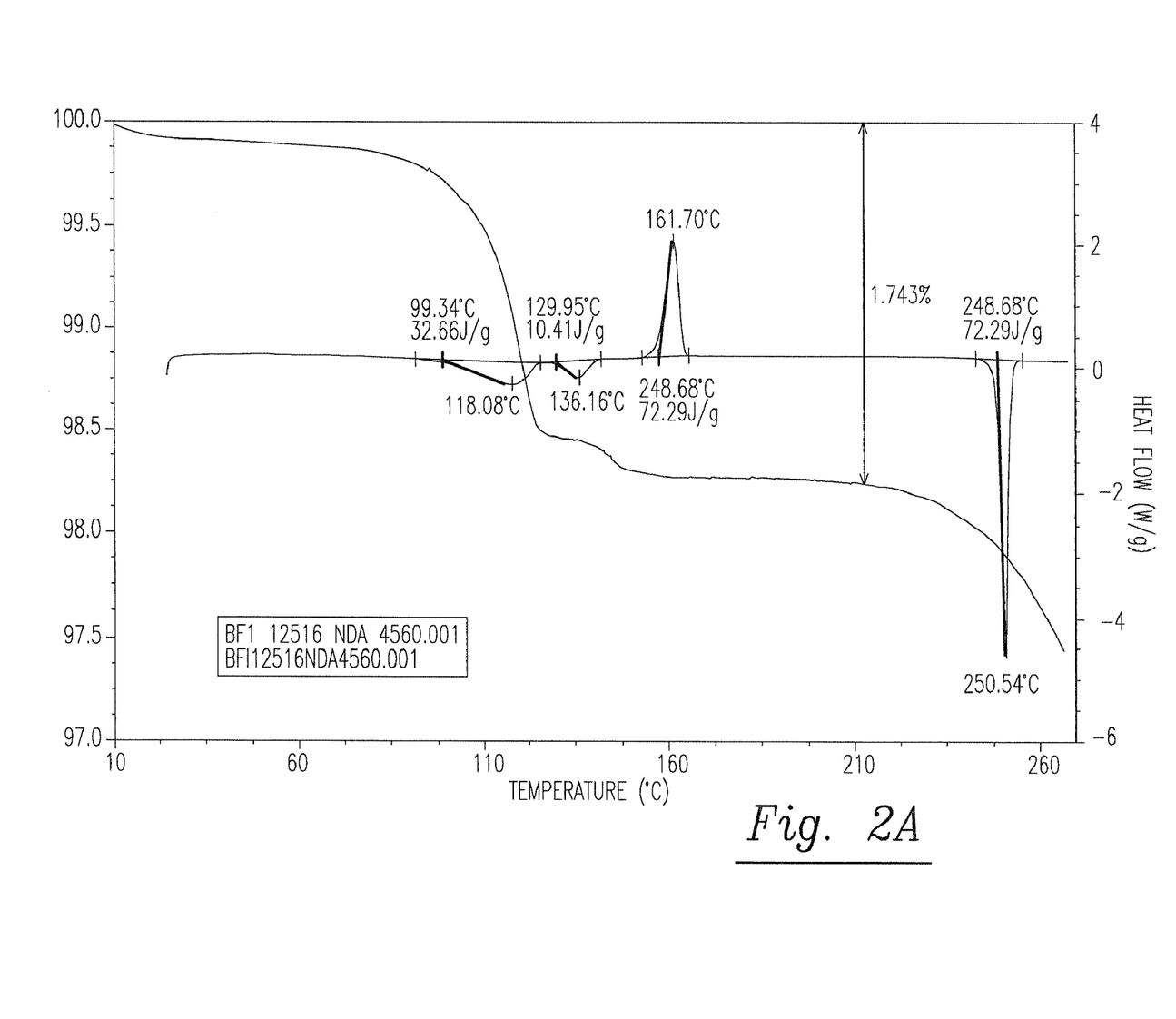
FIG. 2 shows an infrared spectrum of crystalline Form III of Dutasteride.
Figure 2B:
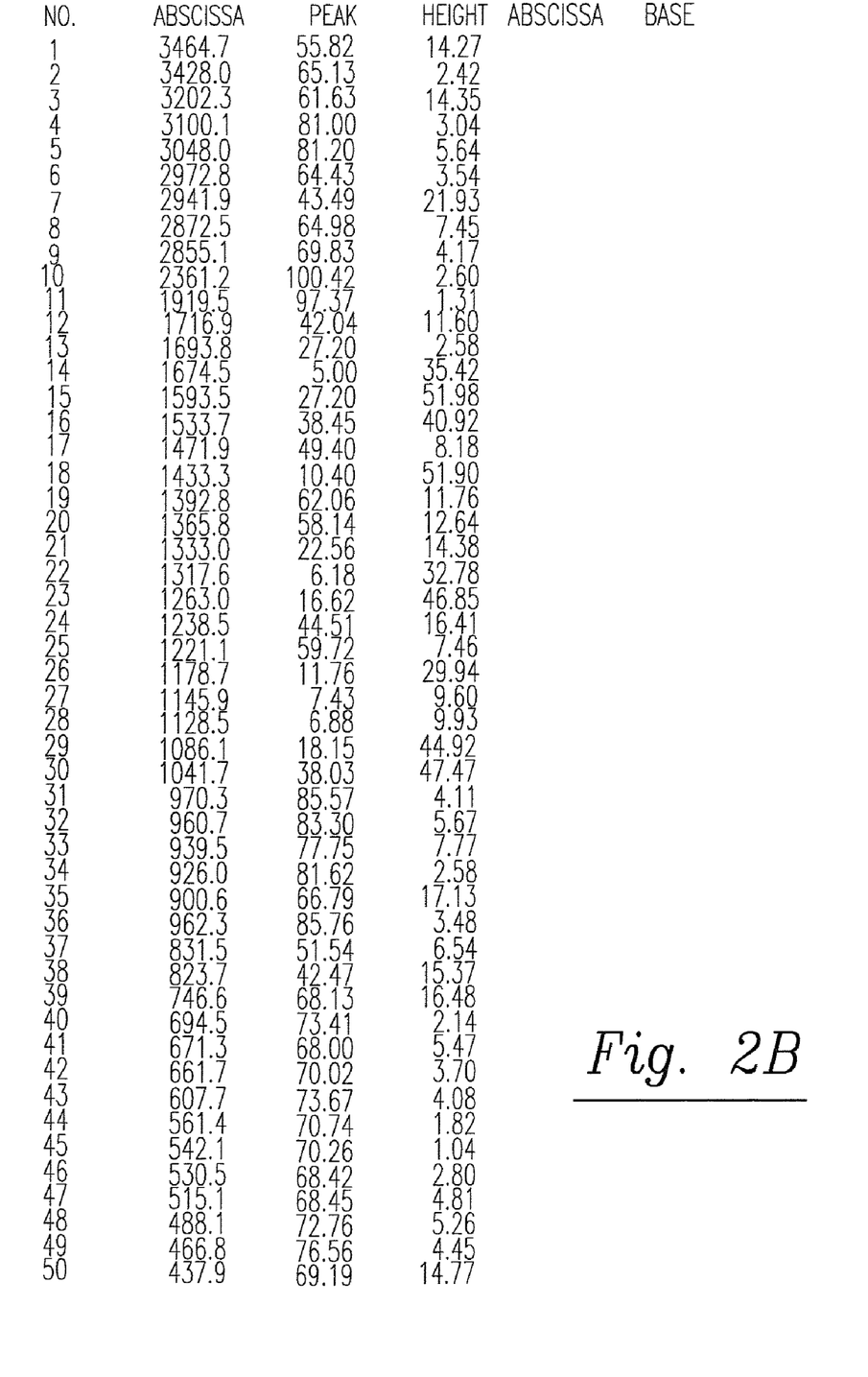
Figure 3:
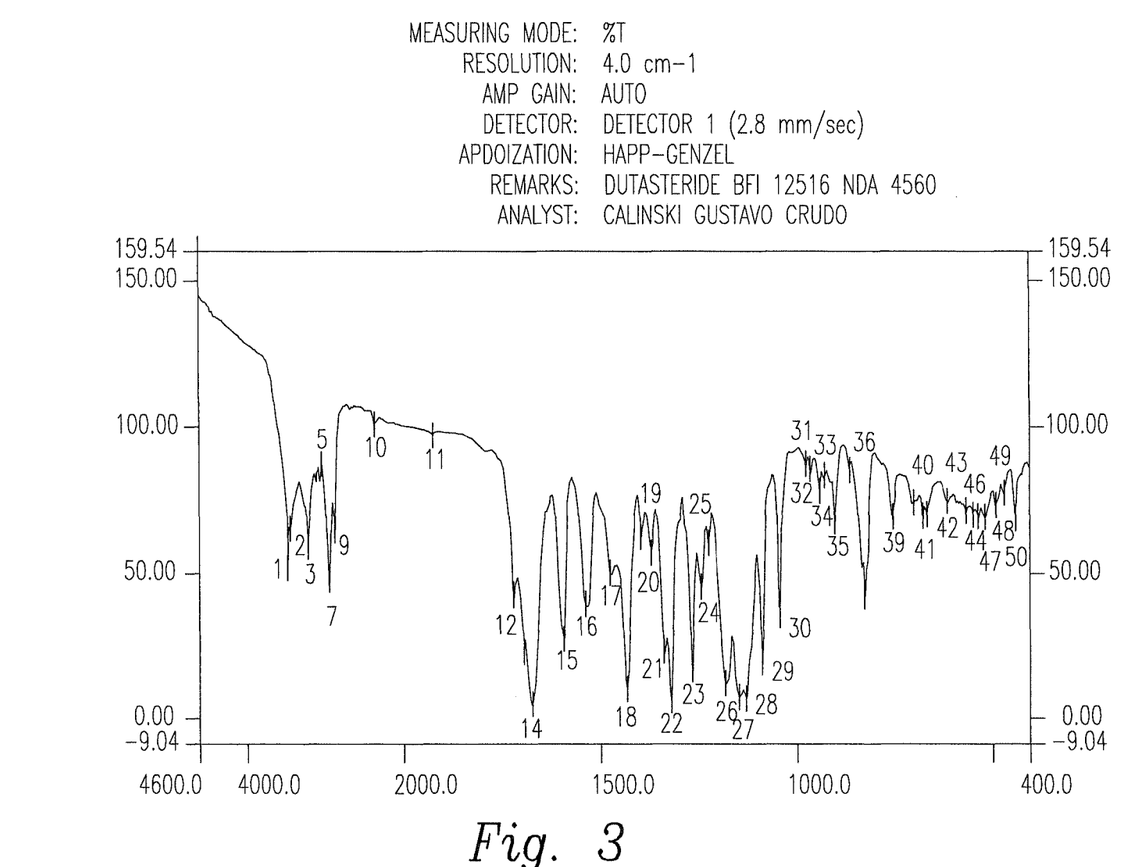
FIG. 3 shows a thermal profile (DSC and TG) of crystalline Form III of Dutasteride.

The crystalline Form III of Dutasteride obtained in the above process is characterized by its X-ray powder diffraction pattern with peaks in angles of 2θ at the following values: 9.59; 9.90; 14.4; 14.7; 15.6; 19.2; 19.4; 19.8; 20.6; 26.9; 28.5 and 28.9±0.2°. The crystalline Form III of Dutasteride has substantially the same X-ray diffraction pattern as shown in FIG. 1.

The crystalline habit of the Form III of dutasteride, described by optical microscopy, corresponds to small birrefrigent crystals. It presents homogeneous distribution of sizes.

The Crystalline Form III of dutasteride presents an intrinsic dissolving speed value (VDI) of the same magnitude of the crystalline forms described in the previous art. These study has been carried out using Lauril Sodium Sulphate SDS 2% in hydrochloric acid 0.1N 225 ml. as dissolvent. At the established experimental conditions, changes were seen depending on the crystalline or polymorphous structure present. The Crystalline Form II and the amorphous Form did not show any changes during the assay whereas the Form I has shown a transformation into Form III detected in the study chart.

The Crystalline Form II of dutasteride has proved to be stable when exposed to different humidity conditions (66% and 75% HR) during a 60-day period. No changes were observed in the solid Form with XR study, and water content has not suffered any modifications, either (KF initial sample: 1.9, final sample: 2.1).

The Following Terms are Defined as Used Herein.

DBU: 1,8-diazabicyclo[5.4.0]undec-7-ene
THF: tetrahydrofuran
BF3: boron trifluoride
Et2O: diethyl ether The present invention will be described in further detail with reference to Examples. However, it should be understood that the present invention is not restricted by the specific Examples.

Preparation

EXAMPLE 1

Mixed Sulfonic-Carboxylic Anhydrides

A suspension of 5 g (15.75 mmol) of 3-oxo-4-aza-5α-androst-1-ene-17-β-carboxylic acid in dry acetonitrile (85 mL) was cooled to −20° C. Then 2.35 mL (15.75 mmol) of 1,8-diazabicyclo[5.4.0]undec-7-ene (DBU) and 1.35 mL (17.33 mmol) of methanesulfonyl chloride were added. The reaction was completed in 15 min. After that, 2.02 ml (12.60 mmol) of boron trifluoride etherate and 2.46 mL (15.75 mmol) of 2,5-bis(trifluoromethyl)aniline were added. The reaction mixture was heated under reflux (76-78° C.) for 4 h. The reaction completion may be monitored by in-process control (HPLC). After cooling, the solution was concentrated in vacuo. The organic residue was dissolved in ethyl acetate (100 mL) and was washed with 5% $NaHCO_3$ solution (3×35 mL) until pH 8.5. The organic solution was washed with 0.1N hydrochloric acid (2×20 mL) and then with water (4×35 mL). The resulting solution was concentrated in vacuum. The solid was dissolved in acetonitrile (92 mL) at reflux. The solution was cooled to 0° C. for 1 h., filtered and washed with acetonitrile (5 mL). The wet solid was dried to 60° C. until to constant weight to offer 5.49 g of Dutasteride (yield: 70%)

EXAMPLE 1a

Mixed Sulfonic-Carboxylic Anhydrides

A suspension of 70 g (220.54 mmol) of 3-oxo-4-aza-5α-androst-1-ene-17-β-carboxylic acid in dry acetonitrile (700 mL) was cooled to −20° C. Then 39.5 mL (264.65 mmol) of 1,8-diazabicyclo[5.4.0]undec-7-ene (DBU) and 18.9 mL (242.6 mmol) of methanesulfonyl chloride were added. The reaction was completed in 30 min. After that, 110.09 ml (882.17 mmol) of boron trifluoride etherate and 34.4 mL (220.54 mmol) of 2,5-bis(trifluoromethyl)aniline were added. The reaction mixture was heated under reflux (76-78° C.) for 4 h. The reaction completion may be monitored by in-process control (HPLC). After cooling, the solution was concentrated in vacuo. The organic residue was dissolved in ethyl acetate (665 mL) and was cooled to 0-5° C. for 30 minutes. The wet solid was filtered and washed and this procedure was repeated four times. The wet solid was dried to 60° C. until to constant weight to offer 118.6 g of Dutasteride (yield: 70%).

EXAMPLE 2

Mixed Carboxylic Anhydrides

A suspension of 1 g of 3-oxo-4-aza-5α-androst-1-ene-17-β-carboxylic acid (3.15 mmol) in dry tetrahydrofurane (19 mL) was cooled to 0° C. and were added 0.47 mL (3.15 mmol) of DBU and 0.47 mL (3.78 mmol) of pivaloyl chloride. The reaction mixture was stirred for 30 min. After that 0.40 ml (2.52 mmol) of boron trifluoride etherate and 0.6 mL (3.78 mmol) of 2,5-bis(trifluoromethyl)aniline were added. The reaction mixture was heated to reflux (65° C.) for 13 h. The solid was isolated following the work-up described in Example 1. Dutasteride 1.13 g were obtained (yield: 70%)

EXAMPLE 3

Form III Dutasteride 5.0 grams of Dutasteride were dissolved in 225 mL of acetonitrile under reflux. The solution was dropped to ice-water during 5 min. The separated solid was filtered and washed with 25 mL of acetonitrile. The obtained solid was dried al 60° C. until constant weight to get the desired crystalline Form III of Dutasteride. (4.59 g., 92% of yield)

Now that the invention has been described,

What is claimed is:

1. A process to prepare crystalline Dutasteride Form III, comprising the following steps:
    a. reacting 4-aza-5α-androst-1-ene-3-one-17β-carboxylic acid with at least one acyl halide selected from the group consisting of methansulfonyl chloride, p-toluensulfonyl chloride and pivaloyl chloride in an aprotic solvent and in the presence of a scavenger of HCl at a temperature below 10° C.;
    b. reacting the intermediate substances generated in the step a. with 2,5-bis(trifluoromethyl)aniline in the presence of a Lewis acid;
    c. heating to reflux until reaction complete;
    d. distilling the solvent to obtain a solid residue or a concentrated solution;
    e. adding water to the concentrated solution obtained in d. to produce a suspension;
    f. filtering the suspension to obtain a solid;
    g. dissolving the solid in organic solvent after that water is added to obtain a suspension;
    h. filtering the suspension and drying the solid;
    i. dissolving the solid residue obtained in d. in an organic solvent, then washing the organic phase with an aqueous solution to eliminate inorganic impurities;
    j. distilling the solvent of organic phase i. to obtain a suspension; and
    k. filtering the suspension obtained in j. and drying the solid.

2. The process according to claim 1, wherein the molar ratio in step a. of acyl halide: 3-oxo-4-aza-5α-androst-1-ene-17-β-carboxylic acid is from 1 to 2:1.

3. The process according to claim 1, wherein the molar ratio in step a. of methansulfonyl chloride: 3-oxo-4-aza-5α-androst-1-ene-17-β-carboxylic acid is from 1 to 2:1.

4. The process according to claim 1, wherein the molar ratio in step a. of pivaloyl chloride: 3-oxo-4-aza-5α-androst-1-ene-17-β-carboxylic acid is from 1 to 2:1.

5. The process according to claim 1, wherein the molar ratio in step a. of p-toluensulfonyl chloride: 3-oxo-4-aza-5α-androst-1-ene-17-β-carboxylic acid is from 1 to 2:1.

6. The process according to claim 1, wherein the scavenger of HCl is selected from pyridine, 1,8-diazabicyclo[5.4.0]undec-7-ene (DBU) and triethylamine, and wherein the molar ratio in step a. of scavenger of HCl:3-oxo-4-aza-5α-androst-1-ene-17-β-carboxylic acid is from 0.5 to 2:1.

7. The process according to claim 6, wherein the molar ratio in step a. of 1,8-diazabicyclo[5.4.0]undec-7-ene (DBU): 3-oxo-4-aza-5α-androst-1-ene-17-β-carboxylic acid is from 0.5 to 2:1.

8. The process according to claim 1, wherein the aprotic solvent is selected from dimethylformamide, dimethylacetamide, acetonitrile or tetrahydrofuran.

9. The process according to claim 1, wherein the scavenger of HCl is selected from 1,8-diazabicyclo[5.4.0]undec-7-ene (DBU), pyridine or triethylamine.

10. The process according to claim 1, wherein the reaction in step a. is conducted at a temperature between −40 and 10° C., preferably −30 to 0° C., most preferably −20 to 0° C".

11. The process according to claim 1, wherein the molar ratio in step b. of Lewis acid: 3-oxo-4-aza-5α-androst-1-ene-17-β-carboxylic acid is from 0.5 to 5:1.

12. The process according to claim 1, wherein the molar ratio in step b. of Lewis acid selected from $BF_3$ or $BCl_3$ or $AlCl_3$ or $TiCl_4$: 3-oxo-4-aza-5α-androst-1-ene-17-β-carboxylic acid is from 0.5 to 5:1.

13. The process according to claim 1, wherein the molar ratio in step b. of Lewis acid, boron trifluoride etherate: 3-oxo-4-aza-5α-androst-1-ene-17-β-carboxylic acid is from 0.5 to 5:1.

14. The process according to claim 1, wherein the molar ratio in step b. of 2,5-bis(trifluoromethyl)aniline: 3-oxo-4-aza-5α-androst-1-ene-17-β-carboxylic acid is from 1 to 2:1.

15. The process according to claim 1, wherein the reaction in step c. is conducted at a temperature between 20 and 90° C.

16. The process according to claim 1, wherein the reaction in step c. is conducted at a temperature between 65 and 77° C.

17. The process, in accordance with claim 1, where the concentrated solution is treated with water in order to obtain a suspension of the product.

18. The process in accordance with claim 1, where the solid obtained in step lf is dissolved in an organic solvent, preferably reflux in acetonitrile.

19. The process in accordance with claim 1, where the solution obtained in step g. is treated with water to obtain solid precipitation.

20. The process according to claim 1, wherein the residue obtained in step d. is dissolved in an organic solvent.

21. The process according to claim 1, wherein the organic layer obtained in step e. is washed with alkaline aqueous solutions by means of an aqueous solution of hydroxides or carbonates of alkaline metals, preferably sodium bicarbonate.

22. The process according to claim 1, wherein the organic layer obtained in step e. is washed with inorganic acid aqueous solutions preferably an aqueous solution of hydrochloric acid.

23. The process according to claim 1, wherein the organic solution obtained in step e. is concentrated by distillation at reduced pressure.

24. The process according to claim 1, wherein the suspension obtained in steps e., g., and j. is filtered and the solid is dried.

25. A novel polymorphic form of Dutasteride, called form III and having:
    an X-ray powder diffraction pattern with peaks in angles of 2θ at the following values: 9.59; 9.90; 14.4; 14.7; 15.6; 19.2; 19.4; 19.8; 20.6; 26.9; 28.5 and 28.9±0.2°;
    a Differential Scanning Calorimetry curve showing one endotherm at 250° C., which corresponds to the melting process; and
    an Infrared Spectrum (KBr) Absorption at 3464, 3202, 2942, 1674, 1593, 1534, 1433, 1318, 1264, 1086, 1042, 824 $cm^{-1}$.

26. A process to prepare crystalline Dutasteride Form III according to claim 25, comprising:
(a) dissolving Dutasteride in a solvent at an elevated temperature to obtain a concentrate; and
(b) progressively contacting the solution of step (a) with a lower temperature phase to crystallize Dutasteride.

27. The process as in claim 26, further comprising:
(c) further cooling the suspension of step (b), filtering the solid and washing the filtrated solid with organic solvent and
(d) drying the washed solid.

28. The process according to claim 26, wherein the dissolution temperature in step a. is within the range from 40 to 90° C.

29. The process as in claim 26, wherein substantially all crystallization occurs in the step b. within the range of 0 to 25° C.

30. The process as in claim 26, wherein said solvent in step a. is acetonitrile.

31. The process as in claim 26, wherein said solvent in step a. is acetone.

32. The process in accordance with claim 26, where said solvent in step a. is methanol.

33. The process in accordance with claim 26, where said solvent in step a. is tetrahydrofuran.

34. The process according to claim 26, where said solvent in step a. is isopropanol.

35. The process according to claim 26, where said solvent in step a. is dioxane.

36. The process as in claim 26, wherein said second phase in step b. is water.

37. The process as in claim 26, wherein said second phase in step b. is carbonic anhydride.

38. The process as in claim 26, wherein said second phase in step b. is metal or glass.

39. The process as in claim 38, wherein said metal or glass is in the form of a tube.

40. The process as in claim 26, wherein the crystalline Dutasteride Form III correspond to a hemihydrate.

41. The process as in claim 26, wherein thermal analysis (TGA and DSC) of the crystalline Dutasteride shows two endotherm between 99 to 140° C. associated with a loss of mass of around 1.7%, and a melting endotherm followed by decomposition at around 250° C.

42. The process as in claim 26, wherein thermal analysis by DSC of the crystalline Dutasteride shows one endotherm between 160-162° C. associated with a transition phase.

43. The process according to claim 1, wherein the drying of steps h. and k. is at atmospheric pressure or in vacuum and at a temperature from 20 to 80° C.

44. The process according to claim 27, wherein the drying in step (d) is made at the atmospheric pressure and at a temperature from 30 to 60° C.

45. A pharmaceutical composition comprising a polymorphic form III of Dutasteride according to claim 25 as an active ingredient, together with one or more pharmaceutically acceptable vehicles.

* * * * *